United States Patent
Novak et al.

(10) Patent No.: US 7,717,913 B2
(45) Date of Patent: May 18, 2010

(54) RF CAUTERIZATION AND ULTRASONIC ABLATION INSTRUMENT WITH MULTI-HOLE COLLAR AND ELECTRODE MOUNTING SLEEVE

(75) Inventors: Theodore A. D. Novak, Northport, NY (US); Alexander L. Darian, Huntington Station, NJ (US); Dan Voic, Clifton, NJ (US); Scott Isola, Deer Park, NY (US)

(73) Assignee: Misonix, Incorporated, Farmingdale, NY (US)

( * ) Notice: Subject to any disclaimer, the term of this patent is extended or adjusted under 35 U.S.C. 154(b) by 1058 days.

(21) Appl. No.: 10/981,368

(22) Filed: Nov. 4, 2004

(65) Prior Publication Data

US 2005/0143730 A1 Jun. 30, 2005

Related U.S. Application Data

(60) Provisional application No. 60/517,653, filed on Nov. 6, 2003.

(51) Int. Cl.
*A61B 18/18* (2006.01)
*A61B 17/32* (2006.01)
(52) U.S. Cl. .................. 606/49; 606/169
(58) Field of Classification Search .......... 606/41, 606/45–50, 169; 604/22
See application file for complete search history.

(56) References Cited

U.S. PATENT DOCUMENTS

| | | | |
|---|---|---|---|
| 5,013,312 A * | 5/1991 | Parins et al. | 606/37 |
| 5,776,092 A * | 7/1998 | Farin et al. | 604/22 |
| 6,454,757 B1 | 9/2002 | Nita et al. | |
| 6,562,032 B1 * | 5/2003 | Ellman et al. | 606/41 |
| 6,736,814 B2 * | 5/2004 | Manna et al. | 606/50 |
| 7,223,267 B2 * | 5/2007 | Isola et al. | 606/52 |
| 2003/0163131 A1* | 8/2003 | Manna et al. | 606/50 |
| 2005/0027310 A1* | 2/2005 | Yamada et al. | 606/169 |

\* cited by examiner

*Primary Examiner*—Michael Peffley
(74) *Attorney, Agent, or Firm*—R. Neil Sudol; Henry D. Coleman; William J. Sapone

(57) ABSTRACT

A surgical instrument comprises, in accordance with the present invention, an elongate probe, a sleeve, a sleeve extension and at least one cauterization electrode. The probe is an ultrasonic element, serving to convey ultrasonic vibrations (as standing waves) to organic tissues at a surgical site. The probe has a working tip and a longitudinal axis. The sleeve surrounds the probe with the working tip of the probe projecting from a distal or free end of the sleeve. The sleeve extension is disposed at the distal or free end of the sleeve and defines a multiplicity of apertures having respective axes oriented at least substantially parallel to the longitudinal axis. The electrode has a distal or free end removably inserted through one of the apertures.

24 Claims, 1 Drawing Sheet

RF CAUTERIZATION AND ULTRASONIC ABLATION INSTRUMENT WITH MULTI-HOLE COLLAR AND ELECTRODE MOUNTING SLEEVE

BACKGROUND OF THE INVENTION

This invention relates to a medical device and more specifically to an ultrasonic tissue ablation instrument. Even more specifically, this invention relates to an ultrasonic medical treatment device with electrocautery. This invention also relates to an associated medical treatment method.

Many diseases of the brain and spine require surgery to provide the patient with relief. These could include cancer, non-malignant lesions and trauma induced by accidents or physical attack. As a procedure, neurosurgery has been practiced for several millennia. Archeologists have discovered evidence of sophisticated cranial surgery in relics and skulls dating back to Roman times. The tools found have been shown to be remarkably similar to today's designs. Of course, modern science has substantially improved upon the techniques and results obtained in those days.

One of the biggest steps forward occurred approximately 30 years ago with the invention and marketing of the ultrasonic surgical aspirator. This device utilizes a hollow probe or tool that vibrates at frequencies at or above 20 kc with tip amplitudes of up to 300 microns. When the vibrating tip is placed against viable or diseased tissue, the moving tip ablates the cells and causes them to fragment or otherwise emulsify in the irrigation fluid that is being added simultaneously. The emulsified fluid is then aspirated through the hollow probe and deposited in a canister for histological examination or disposal.

The advantage of excising tissue with this device is that the surgeon can remove the lesion in layers almost 5 cells thick. By slowly removing the tumor from the top down, he can clearly see when he is reaching healthy tissue allowing him to stop before substantial collateral damage occurs. This is extremely desirable in brain and spine surgery, where tissue does not regenerate. Gastrointestinal surgeons have used the device as well for lesions of the liver and spleen, for the same reasons.

The required specifications, designs and engineering elements of such ultrasonic aspirators have become well known to the art in the intervening time. Although the technology is mature, several improvements can be made to enhance the ease of use and applicability to a wider range of procedures.

One side effect of any surgery is bleeding when the veins, arteries or capillaries are severed. Ultrasonic surgery is more sparing of blood vessels than knives because the collagen content of the vessels is more resistant to ultrasonic emulsion. However, the capillaries and small vessels will be compromised upon exposure to high amplitude ultrasonic tools. When these vessels are severed or punctured bleeding will of course occur. The surgeon will then be forced to pause the procedure, remove the ultrasonic tool from the site and generally reach for a cauterizing device of some type to close off the bleeder. Once coagulation has been achieved, then the surgeon can grab the ultrasonic tool, reposition it in the wound site and continue the removal of tissue. This situation repeats itself often in the course of the operation, lengthening the time of the procedure and coincidently the risk to the patient. It is therefore desired to find a way to cauterize tissue with the ultrasonic tool in place so the surgeon can stop bleeding with minimal downtime caused by switching tools and positions.

Several improvements to the basic design of the ultrasonic aspirator have been disclosed over the years, which allow some degree of cauterization subsequent to or simultaneously with ultrasonic ablation. Most center on the application of RF cautery currents to the tool or probe itself. This has the effect of turning the ultrasonic tool into a monopolar RF cauterizer.

In a non-ultrasonic RF cauterizer, the tip of the tool is energized with a voltage sometimes exceeding 3000 volts RMS. The frequency of the voltage is very high, in order to prevent cardiac arrest in the patient. These frequencies are generally greater than 500,000 Hertz. In monopolar RF, the tool is one pole of the electrical circuit. The second pole is generally a large piece of metal foil which the patient lays on during the procedure. The bare skin touching the foil makes an effective electrical contact. As the tool touches the tissue and the RF voltage is energized, a complete circuit path is created. The currents are very high, reaching 5 amps in some cases. At these currents, significant joule heating occurs in the tissue, raising the temperature higher than the burning temperature of 42° C. Continued operation dries the tissue by evaporating the water content. Cauterization then occurs. Since the back plate is very large in relation to the tool tip, the current "fans out" as it leaves the tool tip and thereby lowers the current density in the tissue to a point where the temperature rise in the tissue is reduced to that below burning. This minimizes collateral burning and tissue damage.

However, as large as the plate is, some collateral damage occurs away from the bleeder site. This collateral damage cannot be controlled reliably by the physician and is of great concern when operating on the brain. If the damage is too widespread, mental capacity or memory may be affected negatively. In addition, electrical current is forced to flow through viable tissue to the ground plate. Again, neurological damage may occur in some organs that are susceptible to damage due to this current, such as the brain, heart and nerve bundles. Other organs, such as the liver or spleen, are less susceptible to current effects.

Researchers have found a way to minimize or eliminate this current path by designing a tool that includes two electrical poles or contacts. This is called bipolar RF cauterization. Here the current flows between the two poles through the intervening tissue. No current path to the back is allowed. Therefore, the tissue that is damaged is only that caught between the two contacts, which can be very small.

Designers have found a way to add monopolar cautery to ultrasonic devices by connecting one electrical contact to the vibrating tip of the ultrasonic device. Several patents have disclosed concepts and techniques for this, such as U.S. Pat. No. 4,931,047 to Broadwin, et al. Here, the tip of the ultrasonic tool is the single pole that touches the tissue. The surgeon will generally stop ultrasonic vibration and turn on the cautery voltage. Current leaves the tip of the probe and goes through the body to the back plate. This has been shown to be effective in eliminating the need for switching tools to stop bleeding, saving time and effort on the doctor's part. However, all of the detriments of monopolar cautery still exist. Neurosurgeons are especially reticent to allow significant current to flow through brain or spinal cord tissue for fear of inducing neurological damage. In addition, the piezoelectric crystals of the ultrasonic transducer stack must be isolated from the cautery voltage or damage to the transducer or electronics will occur.

OBJECTS OF THE INVENTION

It is an object of the present invention to provide an ultrasonic treatment device or instrument having electrocautery capability.

A further object of the present invention to provide such a device or instrument which is easy to use and which provides reliable cautery effects while minimizing patient risk during an ultrasonic aspiration procedure.

Yet another object of the present invention is to provide a bipolar device or instrument with a capability of varying the distance between the cauterization electrodes.

A related object of the present invention is to provide an associated method which combines ultrasonic ablation with electrocautery in a manner that is easy to use.

These and other objects of the present invention will be apparent from the drawings and descriptions herein. Although every object of the invention is attained in at least one embodiment of the invention, there is not necessarily any single embodiment that achieves all of the objects of the invention.

SUMMARY OF THE INVENTION

A surgical instrument comprises, in accordance with the present invention, an elongate probe, a sleeve, a sleeve extension and at least one cauterization electrode. The probe is an ultrasonic element, serving to convey ultrasonic vibrations (as standing waves) to organic tissues at a surgical site. The probe has a working tip and a longitudinal axis. The sleeve surrounds the probe with the working tip of the probe projecting from a distal or free end of the sleeve. The sleeve extension is disposed at the distal or free end of the sleeve and defines a multiplicity of apertures having respective axes oriented at least substantially parallel to the longitudinal axis. The electrode has a distal or free end removably inserted through one of the apertures.

Pursuant to another feature of the present invention, the apertures of the sleeve extension include a plurality of first apertures and at least one second aperture. The first apertures are angularly spaced from one another by a first angle about the longitudinal axis of the probe, while the second aperture is spaced from each of the first apertures by a respective second angle larger than the first angle. In most cases, this means that the second aperture is located at a distance from each of the first apertures that is greater than the distance between adjacent ones of the first apertures.

Preferably, the electrode is one of a plurality of elongate cauterization electrodes each having a distal end insertable through a respective one of the apertures. The present invention provides the possibility of the user easily and rapidly changing the spacing between the electrodes as circumstances warrant.

Pursuant to a further feature of the present invention, the sleeve extension has an annular form coaxial with the longitudinal axis. Particularly, the extension takes the form of a collar removably connected to the sleeve.

In a preferred embodiment of the present invention, the sleeve is tapered so as to have an external diameter at its distal or free end that is larger than an external diameter of the sleeve at a proximal end thereof.

The electrodes may each be provided with an insulating sheath, the electrodes each having a working cauterization tip projecting at the distal or free end of the respective electrode from the respective sheath. The sheaths have an outer diameter closely matching the inner diameter of the apertures so that the electrodes may be removably attached to the extension or collar simply by inserting the electrode through the apertures and securing the electrodes via a friction or force-lock fit.

A surgical method in accordance with the present invention utilizes a surgical instrument including an elongate probe, a sleeve surrounding the probe, and a sleeve extension disposed at a distal or free end of the sleeve, the extension defining a multiplicity of apertures having respective axes oriented at least substantially parallel to a longitudinal axis of the probe. The method also utilizes at least one elongate cauterization electrode. In the performance of the method, the electrode is attached to the sleeve and the extension so that the electrode traverses one of the apertures with a working tip of the electrode projecting from the extension. Ultrasonic vibratory energy is transmitted via the probe to organic tissues at a surgical site. Radio-frequency electrical current is also transmitted to the surgical site via the electrode. Subsequently the electrode is removed from the one aperture and is then inserted through another of the apertures. Thereafter radio-frequency electrical current is conducted to the surgical site via the electrode.

Where the electrode is one of a plurality of electrodes, the method further comprises attaching the electrodes to the sleeve and the extension so that the electrodes traverse respective ones of the apertures with working tips of the electrodes projecting from the extension to form a first bipolar circuit configuration. The transmitting of radio-frequency electrical current to the surgical site then includes transmitting electrical current via the electrodes in the bipolar circuit configuration. The inserting of the removed electrode through the other aperture forms a second bipolar circuit configuration with the working tips of the electrodes disposed at a different distance from one another than in the first bipolar circuit configuration. The conducting of radio-frequency electrical current to the surgical site via the one electrode then include conducting electrical current via the electrodes in the second bipolar circuit configuration.

The apertures may include a plurality of first apertures and at least one second aperture, where the first apertures are angularly spaced from one another by a first angle about the longitudinal axis and where the second aperture is spaced from each of the first apertures by a respective second angle larger than the first angle. In that case, the removing of the one electrode from the one aperture and the inserting of the removed electrode through the other aperture changes an angle of disposition, or angle subtended, between the electrodes.

Where the extension is an element separate from the sleeve, the method may additionally comprise removing the electrode and the extension from the sleeve.

Where the electrode is provided with an insulating sheath, the inserting of the electrode through the another of the apertures includes forcing the electrode with the sheath through the another of the electrodes in a close-tolerance or friction fit.

A surgical instrument comprises, in accordance with another embodiment of the invention, an elongate probe, at least one elongate cauterization electrode, and means for removably mounting the electrode to the probe. The probe is adapted to convey ultrasonic vibrations to organic tissues at a surgical site. The probe has a working vibration tip and a longitudinal axis, while the electrode has a working cauterization tip. The electrode is mounted at least indirectly to the probe so that the cauterization tip is disposable at any of a plurality of different angular locations about the probe axis and so that the cauterization tip is diposed at least substantially proximately to the vibration tip at each of the locations.

In accordance with another feature of the present invention, the means for removably mounting the electrode to the probe includes means for defining a multiplicity of apertures in a region about the vibration tip, such that the apertures have respective axes oriented at least substantially parallel to the probe axis. The electrode is insertable through each of the apertures.

The means for removably mounting the electrode may include a mounting element such as a collar removably attachable at least indirectly to the probe. The mounting element or collar may itself be removably mounted to a sleeve surrounding the probe.

An RF cauterization and ultrasonic ablation instrument in accordance with the present invention may provide monopolar or bipolar cauterization. In monopolar cauterization only one elongate electrode on the ultrasonic probe is used to conduct current. In that case, preferably only one electrode is mounted to the probe. In bipolar cauterization, the angular or linear spacing of the electrodes may be easily and quickly adjusted at any time, depending on the surgical exigencies as perceived by the surgeon.

Components are designed such that retention is accomplished through friction fits and are temporary in nature, allowing for assembly and disassembly without tools or fasteners.

DETAILED DESCRIPTION OF THE PREFERRED EMBODIMENTS

Figure 1:
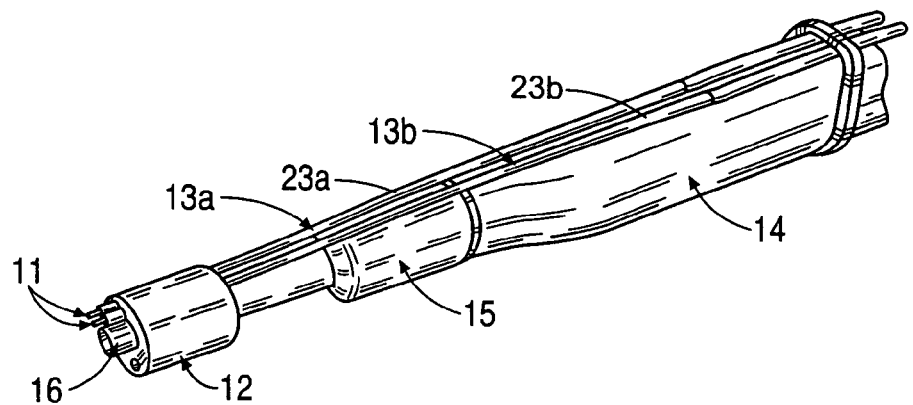
FIG. 1 is a perspective view of a distal end portion of an RF cauterization and ultrasonic ablation instrument in accordance with the present invention.

As depicted in the drawings, a bipolar RF cauterization and ultrasonic ablation instrument comprises an elongate probe 17, a sleeve 15, a sleeve extension 12 and two cauterization electrodes 13a and 13b. Probe 17 is an ultrasonic element, serving to convey ultrasonic vibrations (as standing waves) to organic tissues at a surgical site. The ultrasonic mechanical vibrations are generated by a piezoelectric transducer (not shown) such as that disclosed in U.S. Pat. No. 5,371,429, the disclosure of which is hereby incorporated by reference. The transducer is disposed in a handpiece casing 14 to which probe 17 and sleeve 15 are mounted.

Probe 17 has a working vibration tip 18 and a longitudinal axis 19. Sleeve 15 surrounds probe 17 and defines of central channel or aperture (not designated) receiving the probe, with working probe tip 18 projecting from a distal or free end 16 of the sleeve. Sleeve extension 12 takes the form of a collar, diametrically larger than sleeve 15, that is disposed at the distal or free end 16 of sleeve 15 and defines a multiplicity of apertures 20a, 20b, 20c and 21 having respective axes 22a, 22b, 22c and 22d oriented at least substantially parallel to probe axis 19 the apertures 22a, 22b, 22c, and 21 being located radially farther than sleeve 15 from the probe axis. Electrodes 13a and 13b are removably insertable at their free ends through respective ones of the apertures 20a, 20b, 20c, and 21 so that working cauterization tips 11 of the electrodes project from collar 12 and are disposed in proximity to the vibration tip 18 of probe 17.

Figure 3:
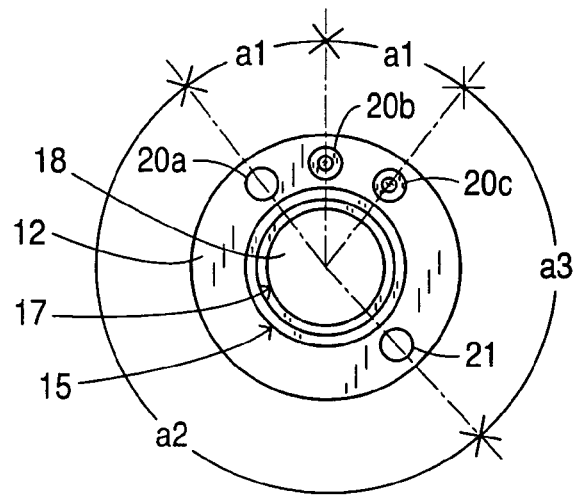
FIG. 3 is a schematic front view of an electrode-mounting collar illustrated in FIGS. 1 and 2.

Apertures 20a, 20b, 20c of collar 12 form a plurality of first apertures that are spaced relative closely to one another. Each adjacent pair of apertures 20a, 20b and 20b, 20c subtend a first angle a1 about probe axis 19, as illustrated in FIG. 3. Aperture 21 is spaced from apertures 20a, 20b, 20c by a distance substantially greater than the distance between the pairs of adjacent apertures 20a, 20b and 20b, 20c. Concomitantly, aperture 21 is spaced at an angle a2 from aperture 20a and an angle a3 from aperture 20c, where angles a2 and a3 are substantially larger than angle a1.

Figure 2:
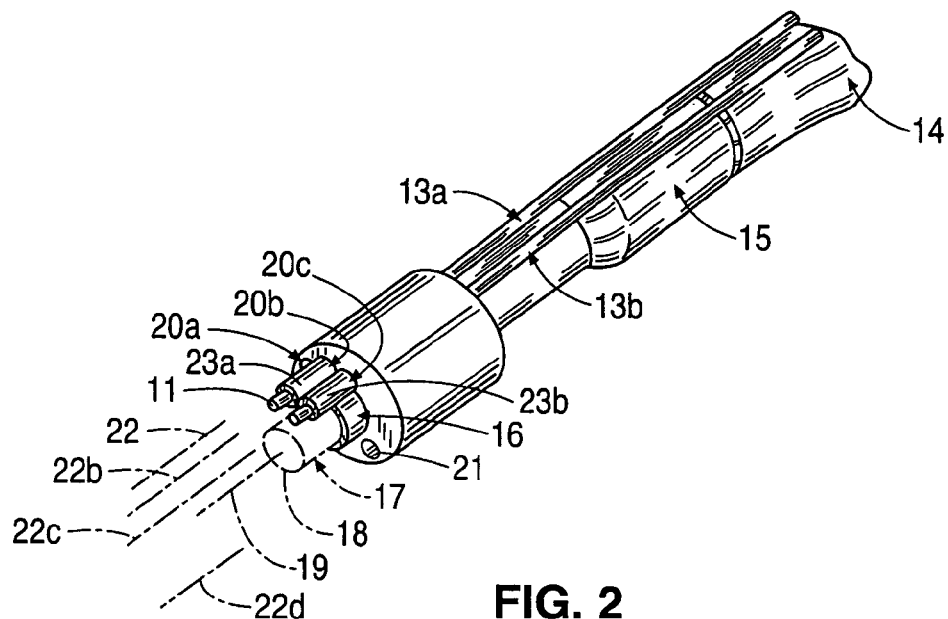
FIG. 2 is a perspective view of the RF cauterization and ultrasonic ablation instrument of FIG. 1, taken at a different angle and on a larger scale.

It is to be understood that only one of the cauterization electrodes 13a and 13b may be used, in which case the instrument of FIGS. 1 and 2 becomes a monopolar cauterization instrument. Where two electrodes 13a and 13b are used, one or both of the electrodes may be moved from one aperture 20a, 20b, 20c, 21 to another to adjust an inter-electrode spacing.

Collar 12 has an annular form coaxial with longitudinal axis 19 of probe 17. Collar is removably slid onto the distal or free end 16 of sleeve 15 and may be maintained there by a friction fit or other connection mechanism.

Sleeve 15 is tapered so as to have an external diameter at its distal or free end 16 that is larger than an external diameter of sleeve 15 at a proximal end thereof.

Electrodes 13a and 13b are each provided with an insulating sheath 23a and 23b and each have a working cauterization tip 11 projecting at the distal or free end of the respective electrode from the respective sheath. Sheaths 23a and 23b have an outer diameter closely matching the inner diameter of apertures 20a, 20b, 20c, 21 so that electrodes 13a and 13b may be removably attached to collar 12 simply by inserting the electrodes through the apertures and securing the electrodes via a friction or force-lock fit.

During use of the instrument of FIGS. 1 and 2, ultrasonic vibratory energy is transmitted via probe 17 to organic tissues at a surgical site for ablating the tissues. Radio-frequency electrical current for cauterization is transmitted to the surgical site via both electrodes 13a and 13b (in a bipolar circuit configuration) or one electrode 13a or 13b (in a monopolar circuit configuration). To change the distance or angular spacing between electrodes 13a and 13b, one or both electrodes are removed from the respective apertures 20a, 20b, 20c, 21 and then inserted through other apertures. Thereafter radio-frequency electrical current is conducted to the surgical site via the remounted electrode(s) 13a, 13b.

Where the electrode is one of a plurality of electrodes, the method further comprises attaching electrodes 13a and 13b to sleeve 15 and the collar 12 so that electrodes 13a and 13b traverse respective ones of the apertures with working tips of electrodes 13a and 13b projecting from the collar 12 to form a first bipolar circuit configuration. The transmitting of radio-frequency electrical current to the surgical site then includes transmitting electrical current via electrodes 13a and 13b in the bipolar circuit configuration. The inserting of the removed electrode through the other aperture forms a second bipolar circuit configuration with the working tips of electrodes 13a and 13b disposed at a different distance from one another than in the first bipolar circuit configuration. The conducting of radio-frequency electrical current to the surgical site via the one electrode then include conducting electrical current via electrodes 13a and 13b in the second bipolar circuit configuration.

Collar 12 (as well as electrodes 13a and 13b) may be removed from sleeve 15 if desired to provide an instrument solely with ultrasonic ablation capability.

The mounting of electrodes 13a and 13b to probe 17 via collar 12 includes inserting the electrodes through respective apertures 20a, 20b, 20c, 21 in a close-tolerance or friction fit.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof

What is claimed is:

1. A surgical instrument comprising:
an elongate probe for conveying ultrasonic vibrations to organic tissues at a surgical site, said probe having a working tip and a longitudinal axis;
a sleeve surrounding at least a distal end portion of said probe with said working tip projecting from a distal or free end of said sleeve;
an extension of said sleeve, disposed at said distal or free end of said sleeve, said extension defining a multiplicity of apertures having respective axes oriented at least substantially parallel to said longitudinal axis; and
at least one elongate cauterization electrode having a distal or free end removably inserted through one of said apertures,
wherein said extension is a collar removably connectable about a distal end portion of said sleeve.

2. The instrument defined in claim 1 wherein said apertures include a plurality of first apertures and at least one second aperture, said first apertures being angularly spaced from one another by a first angle about said longitudinal axis, said second aperture being spaced from each of said first apertures by a respective second angle larger than said first angle.

3. The instrument defined in claim 2 wherein said electrode is one of a plurality of elongate cauterization electrodes each having a distal end insertable through a respective one of said apertures.

4. The instrument defined in claim 3 wherein said extension has an annular form coaxial with said longitudinal axis.

5. The instrument defined in claim 1 wherein said apertures include a plurality of first apertures disposed adjacent to one another and at least one second aperture spaced from said first apertures.

6. The instrument defined in claim 5 wherein said electrode is one of a plurality of elongate cauterization electrodes each having a distal end insertable through a respective one of said apertures.

7. The instrument defined in claim 6 wherein said extension has an annular form coaxial with said longitudinal axis.

8. The instrument defined in claim 1 wherein said electrode has a distal end alternately insertable through each one of said apertures.

9. The instrument defined in claim 1 wherein said extension has an annular form coaxial with said longitudinal axis.

10. The instrument defined in claim 1 wherein said collar has an outer diameter that is substantially larger than an outer diameter of said sleeve, said electrode extending outside said sleeve to said collar.

11. The instrument defined in claim 1 wherein said electrode is provided with an insulating sheath, said electrode having a working tip projecting at the distal or free end of said electrode from the sheath.

12. A surgical method comprising:
providing a surgical instrument including an elongate probe, a sleeve surrounding said probe, and a sleeve extension disposed at a distal or free end of said sleeve, said extension defining a multiplicity of apertures having respective axes oriented at least substantially parallel to a longitudinal axis of said probe;
providing at least one elongate cauterization electrode;
attaching said electrode to said sleeve and said extension so that said electrode traverses one of said apertures with a working tip of said electrode projecting from said extension;
transmitting ultrasonic vibratory energy via said probe to organic tissues at a surgical site;
transmitting radio-frequency electrical current to said surgical site via said electrode;
subsequently removing said electrode from said one of said apertures;
inserting the removed electrode through another of said apertures; and
thereafter conducting radio-frequency electrical current to said surgical site via said electrode.

13. The method defined in claim 12 wherein said electrode is one of a plurality of electrodes, further comprising attaching said electrodes to said sleeve and said extension so that said electrodes traverse respective ones of said apertures with working tips of said electrodes projecting from said extension to form a first bipolar circuit configuration, the transmitting radio-frequency electrical current to said surgical site including transmitting electrical current via said electrodes in said bipolar circuit configuration, the inserting of said removed electrode through said another of said apertures forming a second bipolar circuit configuration with the working tips of said electrodes disposed at a different distance from one another than in said first bipolar circuit configuration, the conducting of radio-frequency electrical current to said surgical site via said one of said electrodes including conducting electrical current via said electrodes in said second bipolar circuit configuration.

14. The method defined in claim 13 wherein said apertures include a plurality of first apertures and at least one second aperture, said first apertures being angularly spaced from one another by a first angle about said longitudinal axis, said second aperture being spaced from each of said first apertures by a respective second angle larger than said first angle, the removing of said one of said electrodes from said one of said apertures and the inserting of the removed electrode through said another of said apertures changing an angle of disposition between said electrodes.

15. The method defined in claim 12 wherein said extension is an element separate from said sleeve, further comprising removing said electrode and said extension from said sleeve.

16. The method defined in claim 12 wherein said electrode is provided with an insulating sheath, the inserting of said electrode through said another of said apertures including forcing said electrode with said sheath through said another of said electrodes in a close-tolerance or friction fit.

17. A surgical instrument comprising:
an elongate probe for conveying ultrasonic vibrations to organic tissues at a surgical site, said probe having a working tip and a longitudinal axis;
a sleeve surrounding at least a distal end portion of said probe with said working tip projecting from a distal or free end of said sleeve;
an extension of said sleeve, disposed at said distal or free end of said sleeve and about a distal end portion of said probe, said extension having an outer surface with a diametrical dimension substantially larger than that of any outer surface said sleeve; and at least one elongate cauterization electrode extending outside of said sleeve, a distal end portion of said electrode passing through an aperture in said extension.

18. The instrument defined in claim 17 wherein said extension is a collar removably connected to said sleeve.

19. The instrument defined in claim 17 wherein said electrode is an elongate rod provided with an insulating sheath, a portion of said electrode proximal of said extension extending along an outer surface of said sleeve.

20. A surgical instrument comprising:

an elongate probe for conveying ultrasonic vibrations to organic tissues at a surgical site, said probe having a working tip and a longitudinal axis;

a sleeve surrounding at least a distal end portion of said probe with said working tip projecting from a distal or free end of said sleeve, said sleeve defining a central aperture or channel receiving said probe;

an extension of said sleeve, disposed at said distal or free end of said sleeve, said extension defining at least three apertures having respective axes oriented at least substantially parallel to said longitudinal axis, said three apertures being located radially farther than said sleeve from said axis; and two elongate cauterization electrodes, at least one of said electrodes having a distal or free end removably inserted through one of said three apertures, another of said electrodes extending through another of said three apertures.

21. The instrument defined in claim 20 wherein said three apertures include two apertures angularly spaced from one another by a first angle about said longitudinal axis, a third of said three aperture being spaced from each of said two apertures by a respective second angle larger than said first angle.

22. A surgical method comprising:

transmitting ultrasonic vibratory energy via an elongate probe to organic tissues at a surgical site;

transmitting radio-frequency electrical current to said surgical site via an electrode connected to said probe at a first location;

subsequently detaching said electrode from said probe;

thereafter attaching an electrode to said probe at another location spaced from said first location; and thereafter conducting radio-frequency electrical current to said surgical site via the electrode attached to said probe at said second location.

23. The method defined in claim 22 wherein the electrode attached to said probe at said first location in part forms a first bipolar circuit configuration, the electrode attached to said probe at said second location in part forming a second bipolar circuit configuration, the transmitting radio-frequency electrical current to said surgical site via the electrode at said first location including transmitting electrical current via said first bipolar circuit configuration, the transmitting radio-frequency electrical current to said surgical site via the electrode at said second location including transmitting electrical current via said second bipolar circuit configuration.

24. A surgical method comprising:

transmitting ultrasonic vibratory energy via an elongate probe to organic tissues at a surgical site;

transmitting radio-frequency electrical current to said surgical site via a pair of electrodes connected to and spaced from said probe, said electrodes being spaced from one another by a first distance; and thereafter conducting radio-frequency electrical current to said surgical site via two electrodes attached to said probe, said two electrodes being spaced from one another by a second distance different from said first distance.

* * * * *